(12) United States Patent
Hirose

(10) Patent No.: US 10,248,766 B2
(45) Date of Patent: Apr. 2, 2019

(54) SIMULATION METHOD AND ANALYZING DEVICE

(71) Applicant: Sumitomo Heavy Industries, Ltd., Tokyo (JP)

(72) Inventor: Ryouta Hirose, Kanagawa (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 501 days.

(21) Appl. No.: 14/228,988

(22) Filed: Mar. 28, 2014

(65) Prior Publication Data

US 2014/0214381 A1 Jul. 31, 2014

Related U.S. Application Data

(63) Continuation of application No. PCT/JP2012/003364, filed on May 23, 2012.

(30) Foreign Application Priority Data

Sep. 29, 2011 (JP) .................................. 2011-213712

(51) Int. Cl.
*G06F 17/50* (2006.01)
*G06F 19/00* (2018.01)

(52) U.S. Cl.
CPC ........ *G06F 19/701* (2013.01); *G06F 17/5009* (2013.01); *G06F 2217/10* (2013.01); *G06F 2217/16* (2013.01)

(58) Field of Classification Search
CPC ............... G06F 19/701; G06F 17/5009; G06F 2217/10; G06F 2217/16

USPC ............................................................ 703/6
See application file for complete search history.

(56) References Cited

U.S. PATENT DOCUMENTS 7,590,514 B1 * 9/2009 Olovsson ............ G06F 17/5018
703/6

FOREIGN PATENT DOCUMENTS

| JP | 2000-266634 A | 9/2000 |
|----|---------------|--------|
| JP | 2001-132700 A | 5/2001 |
| JP | 2006-285866 A | 10/2006 |

OTHER PUBLICATIONS

"Discrete particle simulation of particulate systems: Theoretical developments" Zhu et al. Mar. 23, 2007.*

(Continued)

*Primary Examiner* — Saif A Alhija
(74) *Attorney, Agent, or Firm* — Michael Best & Friedrich LLP

(57) ABSTRACT

An analyzing device includes: a particle definition unit configured to define a system including a plurality of particles in a virtual space; a constraint assigning unit configured to assign a constraint to the system defined by the particle definition unit so as to present a flow; and a numerical computation unit configured to numerically compute a governing equation that governs the motion of each particle of the particle system to which the constraint is assigned by the constraint assigning unit. The numerical computation unit identifies particles linked with a disturbance source of the flow. The analyzing device further includes display control unit configured to display identified particles on a display in a mode different from that of the other particles.

16 Claims, 6 Drawing Sheets

(56) References Cited

OTHER PUBLICATIONS

I. Yildirim et al., "The influence of heat input and presence of a wire on vortex shedding behind a cylinder," Proceedings of the 5th European Thermal-Sciences Conference (Eurotherm 2008), May 18-22, Eindhoven, The Netherlands, May 22, 2008, pp. 1-8, XP055162918, retrieved from htttp://repository.tue.nl/663299.

Fotis Sotiropoulos et al., "The three-dimensional structure of confined swirling flows with vortex breakdown," Journal of Fluid Mechanics, vol. 426, Jan. 10, 2001, pp. 155-175, XP055162971, ISSN: 0022-1120, DOI: 10.1017/S0022112000002342.

D. Levesque et al., "Computer 'Experiments' on Classical Fluids. IV. Transport Properties and Time-Correlation Functions of the Lennard-Jones Liquid near its Triple Point'" Phys. Rev.A, vol. 7, No. 5, 1973, p. 1690-1700.

D.C. Rapaport et al., "Eddy Formation in Obstructed Fluid View: A Molecular-Dynamics Study" Phys.Rev.Lett., vol. 57, No. 6, 1986, p. 695-698.

D.C. Rapaport, "Microscale hyrdodynamics: Discrete-particle simulation of evolving flow patterns," Phys.Rev.A, vol. 36, No. 7, 1987, p. 3288-3299.

Koshizuka, "Particle Methods," Calculation Dynamics Lecuture Series 5, Japan Society for Computational Engineering and Science, Maruzen, 2005.

Mitsunao Ikehata, Introduction to Fluid Dynamics for Marine and Ocean Engineering, Japan Ship Technology Research Association, 1993, p. 130.

Maruyama et al., "13th Calculation Dynamics Lecture Meeting Lecture Collection Papers," 2000, p. 389-390.

Masaaki Hikura, Hideo Ohashi, Standard Mechanical Engineering Course 23, Fluid Mechanics (2), Second Chapter, Corona Publishing Co., Ltd, 1996.

Japan Society of Mechanical Engineers ed., Fluid—collection of photos, Maruzen, 1984, p. 4.

Hiroyuki Shinagawa, Chikyu Wakusei Taiki Joran no Nljigen Simluation, Tentai to Space Plasma no Simluation Summer School Text, http://center.stelab.nagoya-u.ac.jp/summer-school/pdf/maegaki.pdf, Sep. 2002, p. 1-8.

Rayleigh-Taylor Fuanteisei, Computer Simulation ni yoru Ryutai Kaiseki (Donyu Hen), Tokyo Institute of Technology, http://www.eto.titech.ac.jp/contents/sub02/index.html, 2008, p. 1-2.

International Search Report issued in Application No. PCT/JP2012/003364, dated Aug. 28, 2012.

International Preliminary Report on Patentability issued in Application No. PCT/JP2012/003364, dated Apr. 1, 2014.

* cited by examiner

FIG.2

| PARTICLE ID | POSITION | VELOCITY | MARKING FLAG |
|---|---|---|---|
| 1 | (10,20,30) | (5,1,0) | 0 |
| 2 | (11,22,20) | (2,3,4) | 0 |
| 3 | (32,21,10) | (3,3,2) | 1 |
| 4 | (15,10,3) | (5,0,0) | 0 |

114

SIMULATION METHOD AND ANALYZING DEVICE

BACKGROUND OF THE INVENTION

1. Field of the Invention

The present invention relates to a simulation method using a particle system and an analyzing device for analyzing a particle system.

2. Description of the Related Art

Methods for computer-based research into phenomena in material science in general based on classical dynamics and quantum mechanics include simulation based on the molecular dynamics method (hereinafter, MD method). The MD method requires less modeling because the property of a material is given by a potential energy function.

For example, attempts have been made to compute a flow around a cylinder using the MD method and visualize a Karman vortex according to velocity vector distribution.

Attempts are also being made to visualize a vortex using a particle method other than the MD method, visualizing pressure distribution or concentration distribution instead of velocity distribution. The finite element method is also used in an attempt to study a vortex by examining vorticity distribution as well as velocity distribution and pressure distribution.

SUMMARY OF THE INVENTION

One embodiment of the present invention relates to a simulation method. The simulation includes simulating a flow using a system including a plurality of particles defined in a virtual space such that particles linked with a disturbance source of the flow in the process of motion are subject to a process different from that of the other particles.

Another embodiment of the present invention relates to an analyzing device. The analyzing device includes: a particle definition unit configured to define a system including a plurality of particles in a virtual space; a constraint assigning unit configured to assign a constraint to the system defined by the particle definition unit so as to present a flow; and a numerical computation unit configured to numerically compute a governing equation that governs the motion of the particles of the particle system to which the constraint is assigned by the constraint assigning unit. The numerical computation unit identifies particles linked with a disturbance source of the flow. The analyzing device further includes a processing unit configured to subject identified particles to a process different from that of the other particles.

Optional combinations of the aforementioned constituting elements and implementations of the invention in the form of methods, systems, computer programs, and recording mediums storing the computer programs may also be practiced as additional modes of the present invention.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 2 shows an exemplary data structure in the particle data storage unit of FIG. 1;

DETAILED DESCRIPTION OF THE INVENTION

The invention will now be described by reference to the preferred embodiments. This does not intend to limit the scope of the present invention, but to exemplify the invention.

Methods are known capable of computing physical quantity such as velocity or pressure in each unit area in a virtual space and visualizing a vortex by presenting the computed physical quantity to users in an eye-friendly manner, using gradation or the like. Such methods are suitable to analyze a constant state but is not suitable to simulate an inherently dynamic phenomenon such as a vortex because it is difficult to know the motion of fluid particles. Such a problem is faced not only in simulation of a vortex but also in simulation of disturbance of a flow in general.

An illustrative need addressed by the embodiment of the present invention is to provide analysis technology capable of facilitating understanding of the motion of particles in a simulation of a flow.

The analyzing device according to an embodiment of the present invention defines a system including a plurality of particles in a virtual space and simulates a flow in the real world by using the system. The analyzing device subjects particles identified as being linked with a source of disturbance in the process of motion to a process different from those particles not linked with the source of disturbance. For example, the analyzing device displays particles linked with the source of disturbance on a display in a mode different from that of the other particles. This facilitates understanding of the motion of particles in fluid analysis.

Figure 1:
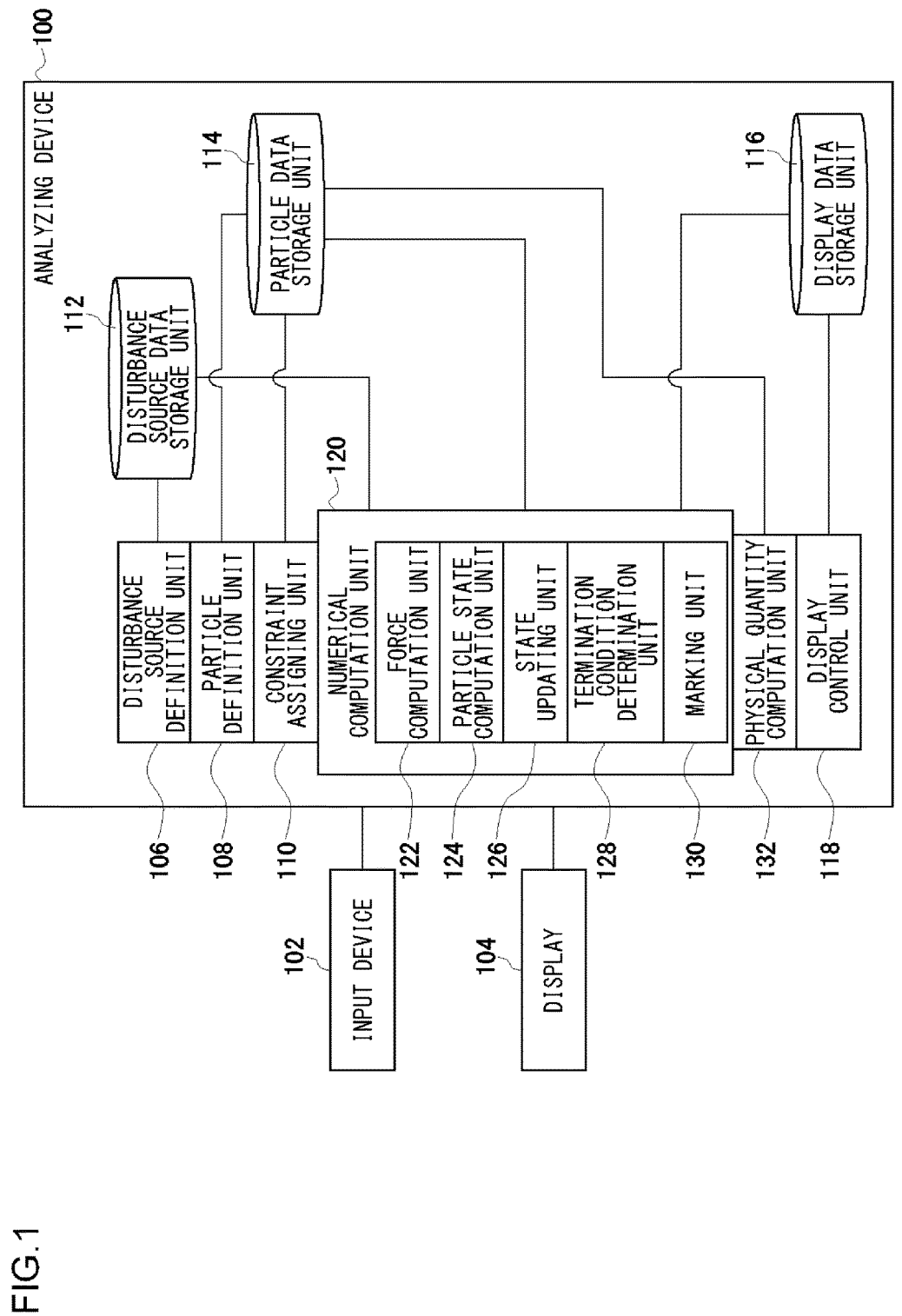
FIG. 1 is a block diagram showing the function and configuration of an analyzing device according to an embodiment.

FIG. 1 is a block diagram showing the function and configuration of an analyzing device 100 according to an embodiment. The blocks depicted in the block diagram are implemented in hardware such as devices or mechanical components such as a CPU of a computer, and in software such as a computer program etc. FIG. 1 depicts functional blocks implemented by the cooperation of these elements. Therefore, it will be obvious to those skilled in the art having accessed this specification that the functional blocks may be implemented in a variety of manners by a combination of hardware and software.

The analyzing device 100 defines a source of disturbance in a flow in a one-dimensional, two-dimensional or three-dimensional virtual space. The analyzing device 100 places a plurality of particles in a virtual space in which the disturbance source is defined and assigns a constraint to the particles so that a flow is presented. The analyzing device 100 simulates a flow in the virtual space including the disturbance source by computing the equation of motion of particles numerically. In particular, the analyzing device 100 according to the embodiment defines a source of generation of a vortex in the virtual space and simulates generation of a vortex caused by the flow.

A description will be given of an embodiment in which a particle system is analyzed according to the MD method.

However, it should be clear to a skilled person having accessed this specification that the technical idea according to the embodiment is applicable to analysis of a particle system according to other particle methods such as renormalized molecular dynamics, distinct element method (DEM), smoothed particle hydrodynamics (SPH), and moving picture semi-implicit (MPS).

The analyzing device 100 is connected to an input device 102 and a display 104. The input device 102 may be a keyboard or a mouse for receiving a user input related to a process performed in the analyzing device 100. The input device 102 may be configured to receive an input from a network such as the Internet or from a recording medium such as a CD, DVD, etc.

The analyzing device 100 includes a disturbance source definition unit 106, a particle definition unit 108, a constraint assigning unit 110, a numerical computation unit 120, a physical quantity computation unit 132, a display control unit 118, a disturbance source data storage unit 112, a particle data storage unit 114, and a display data storage unit 116.

The disturbance source definition unit 106 defines a source of generation of a vortex in a virtual space by referring to input information obtained from the user via the input device 102. At least two approaches are available to define the source. Definition 1: The disturbance source definition unit 106 defines a source of generation of a vortex as an area in the virtual space (hereinafter, referred to as a generation source area). In the computation described below, particles are computed as being subject to a strong repulsive force when entering the generation source area. Definition 2: The disturbance source definition unit 106 places particles coupled to an initial position by a spring (hereinafter, generation source particles) on the surface of the source of generation of a vortex. Whichever definition is employed, the disturbance source definition unit 106 registers data for the source of generation of a vortex as defined in the disturbance source data storage unit 112.

The disturbance source data storage unit 112 stores data for the source of generation of a vortex. In the case that definition 1 is employed to define a source of generation of a vortex, the disturbance source data storage unit 112 stores a parameter and a function to define the generation source area, and a parameter and a function regarding repulsive force. In the case that definition 2 is employed to define a source of generation of a vertex, the disturbance source data storage unit 112 stores an ID identifying generation source particles, the positions of the particles, and the velocities of the particles, mapping the particles, the positions, and the velocities to each other.

The particle definition unit 108 defines a particle system S including N particles (N is a natural number) in a virtual space by referring to input information obtained from a user via the input device 102. The particle definition unit 108 places N particles in the area outside the source of generation of the vortex in the virtual space. The particle definition unit 108 registers the particle IDs identifying the placed particles and the positions of the particles in the particle data storage unit 114, mapping the IDs and the positions to each other. The particles may be mapped to atoms or molecules in the real world.

The constraint assigning unit 110 assigns a constraint to the particle system S defined by the particle definition unit 108 so as to present a flow, by referring to the input information obtained from the user via the input device 102. The constraint assigning unit 110 assigns an initial velocity to the particles so that the particle system S moves in a predefined direction (hereinafter, defined as the direction of flow) as a whole. For example, the constraint assigning unit 110 assigns initial velocities of the same direction and the same magnitude to all particles in the particle system S. The constraint assigning unit 110 registers the particle IDs and the assigned initial velocities in the particle data storage unit 114, mapping the IDs and the velocities to each other.

The constraint assigning unit 110 may assign initial velocities of the same direction and different magnitudes to all particles in the particle system S. Alternatively, the constraint assigning unit 110 may assign an initial velocity to the particles so that the average initial velocity obtained by averaging the initial velocities over the particles (velocity vector) is substantially oriented in the direction of flow. Still alternatively, the constraint assigning unit 110 may assign initial velocities to the particles so that the initial velocity (velocity vector) is oriented in the direction of generation of a vortex.

The description below is directed to a case where the particles in the particle system S are defined as being homogeneous or equivalent and the potential energy function is based on a pair potential and has the identical form independent of the particles. It should be clear, however, to a skilled person having accessed this specification that the technical idea of the present invention is applicable to other cases.

The numerical computation unit 120 numerically computes a governing equation that governs the motion of each particle of the particle system S to which the constraint is assigned by the constraint assigning unit 110. In particular, the numerical computation unit 120 performs computation repeatedly in accordance with the discretized equation of motion of particles. In the process of repeated computation, the numerical computation unit 120 identifies particles linked with the source of generation of a vortex. The numerical computation unit 120 includes a force computation unit 122, a particle state computation unit 124, a state updating unit 126, a termination condition determination unit 128, and a marking unit 130.

The force computation unit 122 refers to the data for the particle system S stored in the particle data storage unit 114 and the data for the source of generation of a vortex stored in the disturbance source data storage unit 112 and computes the force exerted on particles in the particle system S based on the distance between particles. The force computation unit 122 examines the i-th particle ($1 \le i \le N$) of the particle system S and identifies particles for which the distance to the i-th particle is smaller than a predetermined cut-off distance (hereinafter, referred to as proximate particles). The force computation unit 122 computes the force exerted by each of the proximate particles on the i-th particle based on the potential energy function between the proximate particle and the i-th particle and the distance between the proximate particle and the i-th particle. In particular, the force computation unit 122 computes the force by obtaining a value of a gradient of the potential energy function at the value of the distance between the proximate particle and the i-th particle. The force computation unit 122 computes the force exerted on the i-th particle by adding up the forces exerted by all of the proximate particles on the i-th particle.

In case Definition 1 is employed as the definition of the source of generation of a vortex, the force computation unit 122 determines whether the i-th particle of the particle system S is located in the generation source area. If it is determined that the i-th particle is located in the generation source area, the force computation unit 122 adds the repulsive force originated from the source of generation of a vortex to the force exerted on the i-th particle. In case Definition 2 is employed as the definition of the source of generation of a vortex, the force computation unit 122 identifies the proximate particles of the i-th particle, including the generation source particle.

The particle state computation unit 124 refers to the data for the particle system S stored in the particle data storage unit 114 and computes at least one of the position and the velocity of each particle of the particle system S by applying the force computed by the force computation unit 122 to the discretized equation of motion of each particle of the particle system S. In this embodiment, the particle state computation unit 124 computes both the position and velocity of the particles.

The particle state computation unit 124 computes the velocity of the particles using the discretized equation of motion of particles including the force computed by the force computation unit 122. The particle state computation unit 124 computes the velocity of the i-th particle of the particle system S by substituting the force computed by the force computation unit 122 into the discretized equation of motion of the i-th particle, the equation being discretized based on a certain numerical analysis method such as leapfrog method or Euler method and the equation being discretized using a certain minute ticks of time step $\Delta t$. In this computation, the velocity of the particles computed by the previous cycle of repeated computation is used.

The particle state computation unit 124 computes the position of the particle based on the computed velocity of the particle. The particle state computation unit 124 computes the position of the i-th particle of the particle system S by applying the computed velocity of the i-th particle to the equation of the relationship between the position and velocity of the i-th particle, the equation being discretized based on a certain numerical analysis method and the equation being discretized using the ticks of time step $\Delta t$. In this computation, the position of the particles computed by the previous cycle of repeated computation is used.

The state updating unit 126 updates each of the position and velocity of each particle of the particle system S stored in the particle data storage unit 114 with the position and velocity computed by the particle state computation unit 124. The state updating unit 126 also registers the updated data for the particles stored in the particle data storage unit 114 in the display data storage unit 116 along with information dependent on the number of cycles of repeated computation. The information dependent on the number of cycles of repeated computation corresponds to time elapsed in the time evolution of the particle system S. The display data storage unit 116 stores the information corresponding to time elapsed in the time evolution of the particle system S and the data for the particles of the particle system S, mapping the information to the data.

The termination condition determination unit 128 determines whether the repeated computation in the numerical computation unit 120 should be terminated. The repeated computation may be terminated when the computation is repeated a predetermined number of times or when an instruction for termination is received from outside. When the condition for termination is met, the termination condition determination unit 128 terminates the repeated computation in the numerical computation unit 120. The termination condition determination unit 128 returns the process to the force computation unit 122 when the condition for termination is not met. This causes the force computation unit 122 to compute the force at the position of the particle updated by the state updating unit 126.

The marking unit 130 marks the particles linked with the source of generation of a vortex in one of the two following modes. First mode: The marking unit 130 marks the particles entering the interface layer of the source of generation of a vortex in the process of repeated computation. The interface layer is described in detail in, for example, "Mitsunao Ikehata, Introduction to Fluid Dynamics for Marine and Ocean Engineering, Japan Ship Technology Research Association, 1993, p. 130" and "Masaaki Hikura, Hideo Ohashi, Standard Mechanical Engineering Course 23, Fluid Mechanics (2), Second Chapter, Corona Publishing Co., Ltd, 1996" so that only a brief description will be given below.

According to the aforementioned documents, the ratio between the representative length l of a disturbance source and the thickness δ of an interface layer is proportional to the Reynolds number R raised to minus 0.5.

$$\frac{\delta}{l} \propto \frac{1}{\sqrt{Re}}$$

For example, the thickness δ of the interface layer in the case of a flat sheet is given by:

$$\delta = \frac{5l}{\sqrt{Re}}$$

The marking unit 130 marks the particles at a desired point of time in a given cycle of repeated computation in the numerical computation unit 120. The marking unit 130 may mark the particles when the state updating unit 126 updates the particle data storage unit 114 or marks the particles before the computation by the force computation unit 122.

The marking unit 130 determines the interface layer by referring to the data for the source of generation of a vortex stored in the disturbance source data storage unit 112. The marking unit 130 refers to the particle data storage unit 114 and determines whether each of the particles of the particle system S enters the interface layer. When it is determined that the particle enters the interface layer, the marking unit 130 turns on a marking flag mapped by the particle data storage unit 114 to the particle ID of the particle. If the marking flag is already turned on, the marking unit 130 maintains the flag. The marking flag assumes a value "0" or "1". When the flag is "1", it means that the marking flag is turned on. When the flag is "0", it means that the marking flag is turned off.

Second mode: The marking unit 130 marks the particles that have interacted with the source of generation of a vortex in the process of repeated computation.

In the case that definition 1 is employed as the definition of the source of generation of a vortex, the marking unit 130 refers to the particle data storage unit 114 and the disturbance source data storage unit 112 and determines whether each of the particles of the particle system S comes into contact with the generation source, i.e., whether the particle enters the generation source area. If it is determined that the particle enters the generation source area, the marking unit 130 turns on the marking flag mapped by the particle data storage unit 114 to the particle ID of the particle.

In the case that definition 2 is employed as the definition of the source of generation of a vortex, the marking unit 130 refers to the particle data storage unit 114 and the disturbance source data storage unit 112 and determines whether the generation source particle exerts a force on each of the particles of the particle system S. In particular, the marking unit 130 examines each of the particles of the particle system S and determines whether there is any generation source particle for which the distance to the particle is smaller than the cut-off distance. If it is determined that there is such a generation source particle, the marking unit 130 turns on the marking flag mapped by the particle data storage unit 114 to the particle ID of the particle.

The process performed by the marking unit 130 in the second mode may be built in the process in the force computation unit 122.

The analyzing device 100 subjects the particles identified by the numerical computation unit 120 to a process different from the process applied to the other particles. For example, the physical quantity of the identified particles may be computed independently of the computation on the other particles. Alternatively, the identified particles and the other particles may be displayed on the display 104 in different modes.

The physical quantity computation unit 132 computes the physical quantity (e.g., the temperature, pressure, stress, vorticity) of the particle system S by referring to the data for the particle system S stored in the particle data storage unit 114. In this process, the physical quantity computation unit 132 may perform computation on the particles for which the marking flag is turned on separately from the other particles. Alternatively, the physical quantity computation unit 132 may compute the physical quantity only on the particles for which the marking flag is turned on or compute the physical quantity only on the other particles.

The display control unit 118 displays the time evolution of the particle system S or the state occurring at a certain point of time on the display 104, by referring to the position, velocity, marking flag of the particles of the particle system S stored in the display data storage unit 116. The display control unit 118 may display still images or moving images. In particular, the display control unit 118 displays the particles for which the marking flag is turned on in a manner different from that of the other particles.

For example, the display control unit 118 may display on the display 104 only the particles for which the marking flag is turned on. Alternatively, the display control unit 118 may display on the display 104 only the particles for which the marking flag is turned off. This reduces the number of particles that should be displayed so that the display of particles is not less likely to be constrained by the hardware performance. Alternatively, the display control unit 118 may display the particles for which the marking flag is turned on in a color different from that of the other particles. Still alternatively, the display control unit 118 may additionally display a contour dependent on the vorticity computed by the physical quantity computation unit 132. This facilitates analysis of the vortex generated by the flow.

FIG. 2 shows an exemplary data structure in the particle data storage unit 114. The particle data storage unit 114 stores particle IDs, positions of particles, velocities of particles, and marking flags, mapping the data to each other.

In the embodiment described above, the storage unit is exemplified by a hard disk or a memory. It will be understood by a skilled person having accessed this specification that certain units of the device may be implemented by a CPU (not shown), a module of an application program installed in the device, a module of a system program, a memory temporarily storing data read from a hard disk, etc.

A description will be given of the operation of the analyzing device 100 according to the embodiment.

Figure 3:
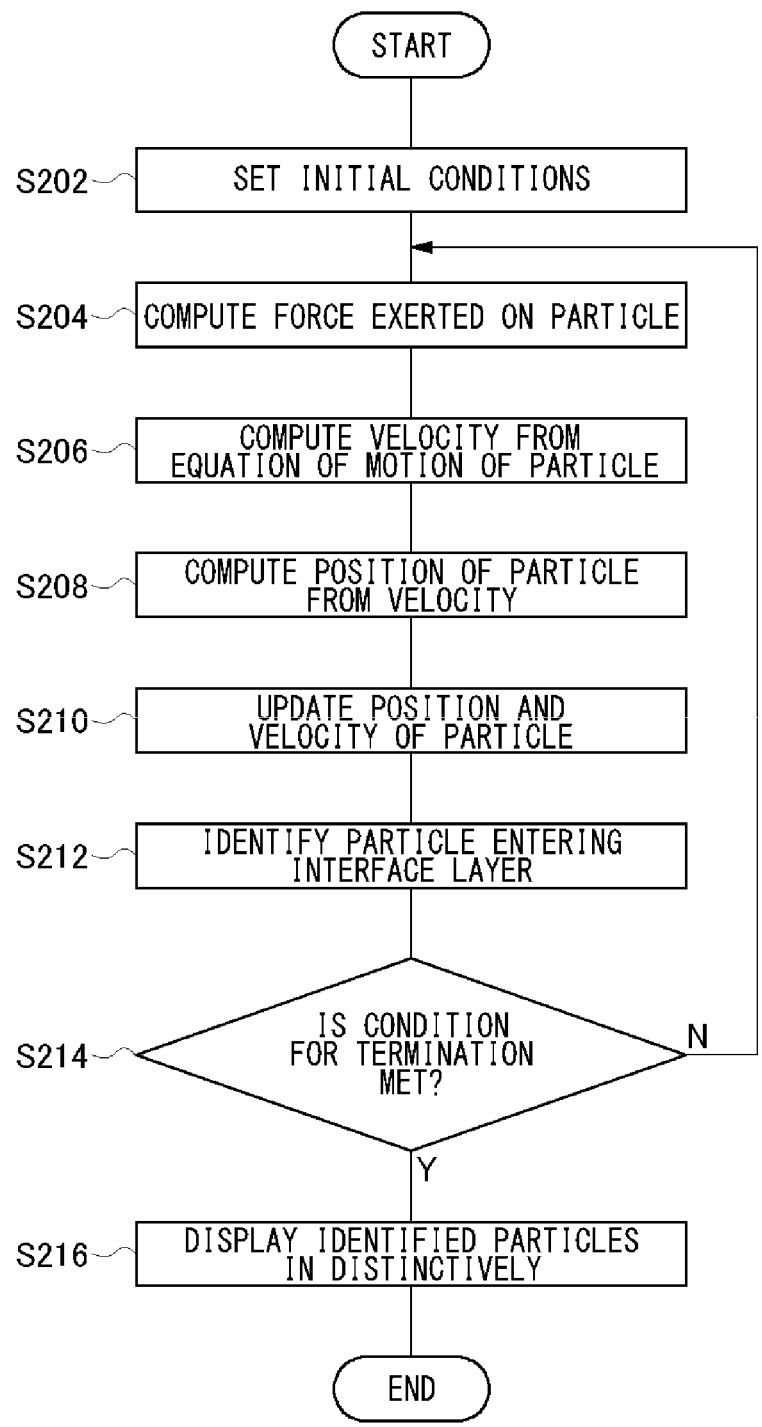
FIG. 3 is a flowchart showing a series of exemplary steps performed by the analyzing device of FIG. 1.

FIG. 3 is a flowchart showing a series of exemplary steps performed by the analyzing device 100. FIG. 3 shows a case in which the first mode is used in the marking unit 130. The disturbance source definition unit 106, the particle definition unit 108, and the constraint assigning unit 110 define initial conditions that include a model of the source of generation of a vortex, the particle system S, and the initial positions and initial velocities of the particles (S202). The force computation unit 122 computes the force exerted on the particles by referring to the distance between particles (S204). The particle state computation unit 124 computes the velocity using the equation of motion of particles including the computed force (S206). The particle state computation unit 124 computes the position of the particle by referring to the computed velocity (S208). The state updating unit 126 updates the position and velocity of the particles stored in the particle data storage unit 114 with the position and velocity computed by the particle state computation unit 124. The marking unit 130 refers to the updated data for particles stored in the particle data storage unit 114 and identifies particles newly entering the interface layer. The termination condition determination unit 128 determines whether the condition for termination is met (S214). If the condition for termination is not met (N in S214), the process is returned to S204. If the condition for termination is met (Y in S214), the display 104 displays identified particles in a distinguishable manner (S216).

According to the analyzing device 100 of the embodiment, particles linked with the source of generation of a vortex in the process of repeated computation are identified. The particles identified as such are processed in a mode different from that of the other particles. Accordingly, the action exerted by the source of generation of a vortex on the flow can be simulated more accurately than in the related art.

The particles linked with the source of generation are displayed on the display 104 in a mode different from that of the other particles so that the vortex can be visualized more accurately than otherwise. Further, the motion of fluid particles as well as the position and size of the vortex can be understood more easily than otherwise.

Known experimental methods to visualize a flow include the suspension method and the electrolytic precipitation method (see, for example, "Japan Society of Mechanical Engineers ed., Fluid—collection of photos, Maruzen, 1984, p. 4"). We have come to an idea of simulating a flow, visualizing it like the electrolytic precipitation method and so devised the analyzing device 100 according to the embodiment. The electrolytic precipitation method uses white precipitation generated in the neighborhood of the anode when, for example, electrolyzing water, as a tracer. We have conceived of an idea of more effectively visualizing a vortex after the fashion of the electrolytic precipitation method by referring to whether an interaction with the interface layer of the source of generation of a vortex or with the generation source takes place for determination as to whether the particle should be marked.

Particles exhibiting properties different from those of the particles of the particle system S may be initially introduced in the particle system S after the fashion of the suspension method so that the flow is simulated by tracking those heterogeneous particles. However, the approach according to the embodiment is different from the methods based on the suspension method at least in that the particles linked with the source of generation of a vortex in the process of motion are identified. In the approach according to the embodiment, heterogeneous particles are not introduced into the particle system S. Thus, in accordance with the method of the embodiment, the particle system S is not disturbed by introducing heterogeneous particles so that the flow can be simulated more accurately. In the method in which heterogeneous particles are introduced, heterogeneous particles are observed in portions not relevant to the vortex. In contrast, particles linked with the source of generation of a vortex are identified by the approach according to the embodiment. Therefore, the latter method should show the state of a vortex more clearly than the former method when the vortex is visualized.

Figure 4:
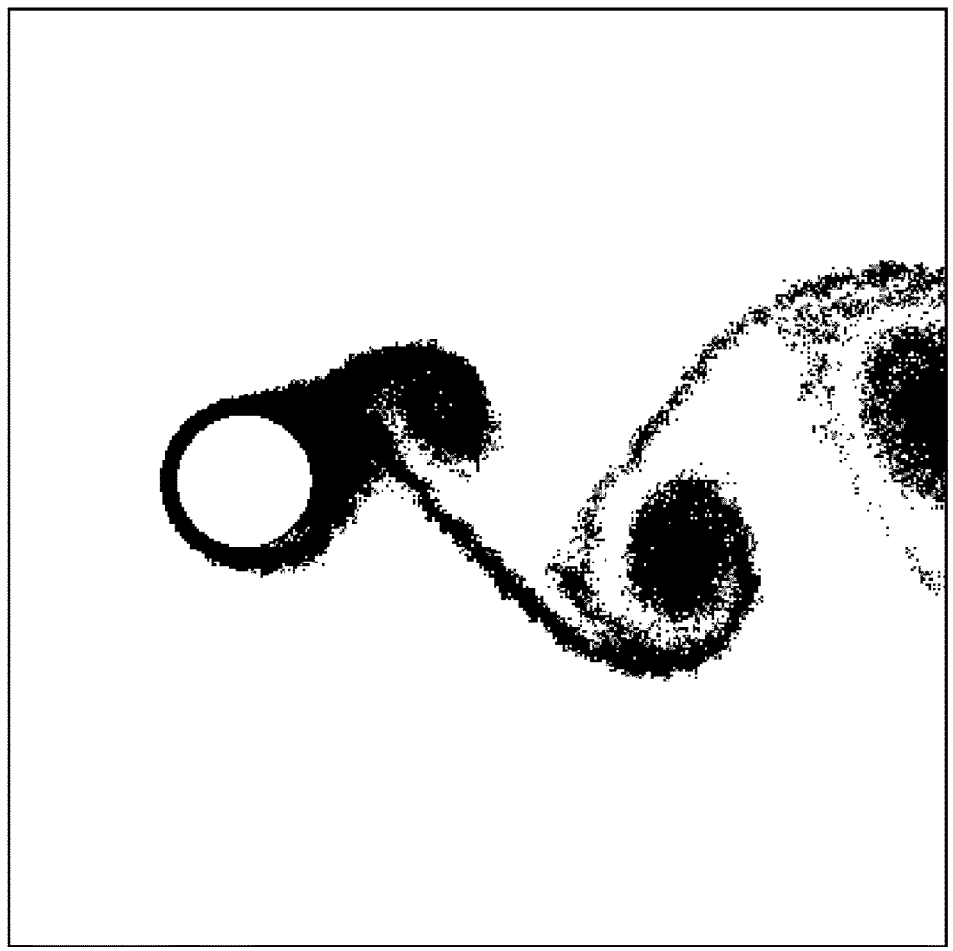
FIG. 4 is a typical image of an exemplary result of simulation by the analyzing device of FIG. 1.

FIG. 4 is a typical image of an exemplary result of simulation by the analyzing device 100. FIG. 4 shows only those particles marked by the marking unit 130 as colored. Comparing FIG. 4 with the diagram of a Karman vortex street behind a square cylinder obtained by the electrolytic precipitation method shown in the above-mentioned literature, it is revealed that the approach according to the embodiment simulates the vortex more properly.

We simulated a flow around a cylinder by the MD method and applied the visualization method according to the embodiment in order to validate the advantage of the method according to the embodiment.

Figure 5:
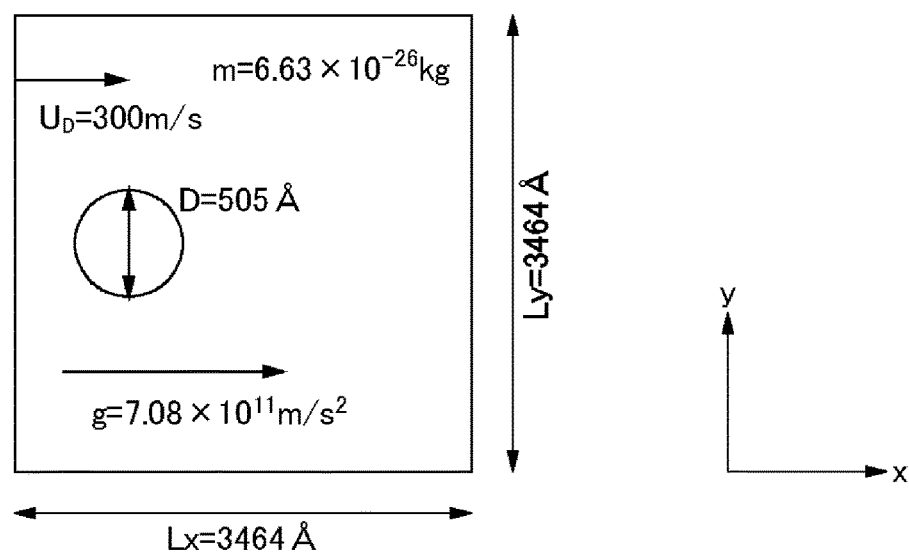
FIG. 5 is a schematic diagram showing conditions for an exemplary computation.

FIG. 5 is a schematic diagram showing conditions for an exemplary computation. A two-dimensional virtual space is defined. The virtual space is defined to be $3464\times10^{-10}$ (m) in the x direction and $3464\times10^{-10}$ (m) in the y direction. The number of particles in the particle system S is defined to be about 800,000, and the weight of a particle is defined to be $6.63\times10^{-26}$ (kg). The diameter of a cylinder is defined to be $505\times10^{-10}$ (m). The inflow temperature is defined to be 85 (K), and the initial velocity in the positive direction of the x axis is defined to be 300 (m/s). Further, the particles are subject to an acceleration of $7.08\times10^{11}$ (m/s$^2$). The acceleration is applied in order to prevent the particles from returning in the negative direction of the x direction due to loss of pressure resulting from the placement of the cylinder. As indicated by the expression (1) below, the interaction between particles is modeled by using only the repulsive term of the Lennard-Jones potential which is often used in the MD method. The potential parameter is defined as indicated by the expression (2) below.

$$\begin{cases} \phi = 4\varepsilon\left\{\left(\frac{\sigma}{\gamma}\right)^{12} - \left(\frac{\sigma}{\gamma}\right)^{6}\right\} + \varepsilon & \left(\gamma \leq 2^{\frac{1}{6}}\sigma\right) \\ \phi = 0 & \left(\gamma > 2^{\frac{1}{6}}\sigma\right) \end{cases} \quad (1)$$

$$\varepsilon = 1.65\times10^{-21}(J) \quad (20$$
$$\sigma = 3.41\times10^{-10}(m)$$

Further, Definition 2 is employed to define the source of generation of a vortex. A generation source particle coupled to the initial position is placed on the surface of the cylinder (in the exemplary computation, on the circumference of a circle because the virtual space defined is two-dimensional). The generation source particle placed on the surface of the cylinder is subject to temperature control by the Langevin method (see "Shigeo Maruyama, Kazuhiro Inoue, Collected Papers of 13th Computational Mechanics Division Conference, 2000, pp. 389-390"). The temperature of the cylinder is defined to be 85 (K).

The viscocity of the particles of the particle system S is defined to be $3.64\times10^{-4}$ (Pa*s) (see "D. Levesque, L. Verlet, J. Kurkijarvi, Phys. Rev. A, 1973, vol 7, no 5, pp. 1690-1700") and the concentration is defined to be $1.18\times10^{3}$ (kg/m$^3$). The representative length is the diameter of the cylinder and is $505\times10^{-10}$ (m). The flow rate as defined by the average velocity in front of the cylinder is 426 (m/s). Therefore, the Reynolds number of the system is 70.1.

Figure 6:
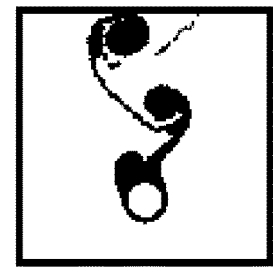
FIG. 6 is a schematic diagram showing time-dependent change of the result of simulation performed under the conditions for the exemplary computation.
Figure 6:
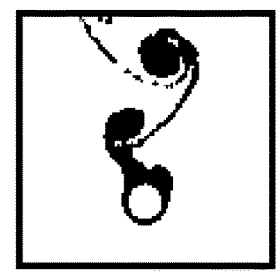
Figure 6:
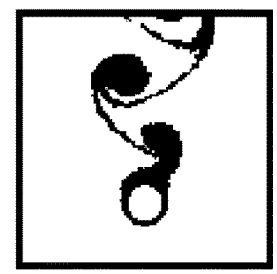
Figure 6:
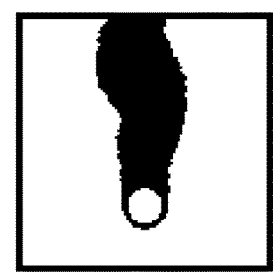
Figure 6:
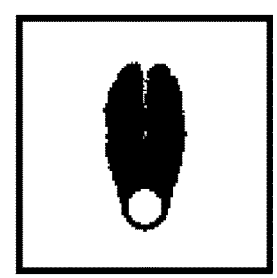

FIG. 6 is a schematic diagram showing time-dependent change of the result of simulation performed under the conditions for the exemplary computation. In FIG. 6, as in FIG. 4, the particles that are marked are shown colored. FIG. 6 demonstrates that the approach according to the embodiment enables visualization as provided by the electrolytic precipitation method using the MD method. Further, as compared with the related-art visualization, the approach according to the embodiment allows understanding of the motion of particles as well as the position and size of the vortex. In other words, the approach according to the embodiment is useful for visualization in fluid analysis.

Described above is the configuration and operation of the analyzing device 100 according to the embodiment. The embodiment is intended to be illustrative only and it will be obvious to those skilled in the art that various modifications to constituting elements and combinations of processes could be developed and that such modifications are also within the scope of the present invention.

The numerical computation unit 120 is described above as computing both the position and velocity of the particles, but this is by way of example only. For example, there are methods, such as the Verlet method, capable of directly computing the position of a particle by referring to the force computed as being exerted on the particle when computing the position of the particle and not requiring positively computing the velocity of the particle. The technical idea of the embodiment may be applied to such a method.

The marking unit 130 in the first mode is described above as marking the particles entering the interface layer of the source of generation of a vortex in the process of repeated computation, but this is by way of example only. An arbitrary layer thinner than the interface layer may be defined and the marking unit may mark the particles entering the defined thin layer in the process of repeated computation.

What is claimed is:

1. An analyzing device for simulating of a flow of particles in a virtual space, the analyzing device comprising:
    disturbance source data storage means configured to electronically store data for a source of a disturbance in the flow of the particles in the virtual space and data for a source of generation of a vortex that is caused by the flow of the particles in the virtual space;
    particle data storage means configured to electronically store positions of the particles in the virtual space and velocities of the particles in the virtual space;
    constraint assigning means configured to electronically assign a constraint to the particles so as to simulate the flow of the particles in the virtual space, the constraint including an initial velocity assigned to each of the particles so that the particles in the virtual space move in a direction of the flow;
    numerical computation means configured to electronically, after the constraint to the particles is assigned by the constraint assigning means, compute a governing equation that governs the motion of said each of the particles; and
    display control means configured to electronically control a display, on a display device, the flow of the particles in the virtual space and the vortex that is caused by the flow of the particles in the virtual space,
    wherein the numerical computation means, by referring to the disturbance source data storage means and the particle data storage means, electronically identifies the particles that are linked with the source of the disturbance in the flow of the particles in the virtual space, and wherein the particles displayable on the display device that the numerical computation means has identified as being linked with the source of the disturbance in the flow in the virtual space are distinguishable on the display device from others of the particles that are displayable on the display device.

2. The analyzing device according to claim 1, wherein the numerical computation means, by referring to the disturbance source data storage means and the particle data storage means, identifies the particles entering an interface layer of the source of the disturbance in the flow of the particles in the virtual space, and wherein the particles displayable on the display device that the numerical computation means has identified as being entering interface layer of the source of the disturbance in the flow in the virtual space are displayable on the display device in a mode distinguishable from the others of the particles.

3. The analyzing device according to claim 1, wherein the numerical computation means, by referring to the disturbance source data storage means and the particle data storage means, identifies the particles that interact with the source of the disturbance in the flow of the particles in the virtual space, and wherein the particles displayable on the display device that the numerical computation means has identified as being interacting with the source of the disturbance in the flow in the virtual space are displayable on the display device in a mode distinguishable from the others of the particles.

4. The analyzing device according to claim 1, further comprising:

particle definition means configured to electronically, before the constraint to the particles is assigned by the constraint assigning means, define a particle system that includes the particles in the virtual space.

5. The analyzing device according to claim 1, wherein the constraint includes a magnitude assigned to said each of the particles so that the particles in the virtual space move in the direction of the flow.

6. A method for simulating of a flow of particles in a virtual space, the method comprising:

electronically, in a disturbance source data storage unit, storing data for a source of a disturbance in the flow of the particles in the virtual space and data for a source of generation of a vortex that is caused by the flow of the particles in the virtual space;

electronically, in a particle data storage unit, storing positions of the particles in the virtual space and velocities of the particles in the virtual space;

electronically, by a constraint assigning unit, assigning a constraint to the particles so as to simulate the flow of the particles in the virtual space, the constraint including an initial velocity assigned to each of the particles so that the particles in the virtual space move in a direction of the flow;

electronically, by a numerical computation unit after the constraint to the particles is assigned by the constraint assigning unit, computing a governing equation that governs the motion of each of the particles; and electronically, by a display control unit, controlling a display, on a display device, the flow of the particles in the virtual space and the vortex that is caused by the flow of the particles in the virtual space, wherein the numerical computation unit, by referring to the disturbance source data storage unit and the particle data storage unit, identifies the particles that are linked with a source of a disturbance in the flow of the particles in the virtual space, and wherein the particles displayed on the display device that the numerical computation unit has identified as being linked with the source of the disturbance in the flow in the virtual space are distinguishable on the display device from others of the particles displayed on the display device.

7. The method according to claim 6, wherein the numerical computation unit, by referring to the disturbance source data storage unit and the particle data storage unit, identifies the particles entering an interface layer of the source of the disturbance in the flow of the particles in the virtual space, and wherein the particles displayable on the display device that the numerical computation unit has identified as being entering interface layer of the source of the disturbance in the flow in the virtual space are displayable on the display device in a mode distinguishable from the others of the particles.

8. The method according to claim 6, wherein the numerical computation unit, by referring to the disturbance source data storage unit and the particle data storage unit, identifies the particles that interact with the source of the disturbance in the flow of the particles in the virtual space, and wherein the particles displayable on the display device that the numerical computation unit has identified as being interacting with the source of the disturbance in the flow in the virtual space are displayable on the display device in a mode distinguishable from the others of the particles.

9. The method according to claim 6, further comprising: electronically, by a particle definition unit before the constraint to the particles is assigned by the constraint assigning unit, defining a particle system that includes the particles in the virtual space.

10. The method according to claim 6, wherein the constraint includes a direction assigned to said each of the particles so that the particles in the virtual space move in the direction of the flow.

11. The method according to claim 6, wherein the constraint includes a magnitude assigned to said each of the particles so that the particles in the virtual space move in the direction of the flow.

12. The method according to claim 6, further comprising: electronically obtaining input information from an input device.

13. The method according to claim 12, wherein the constraint assigning unit assigns the constraint to the particles in the virtual space by referring to the input information.

14. The method according to claim 6, wherein the disturbance source data storage unit and the display control unit are electrically connected to the numerical computation unit, the numerical computation unit and the constraint assigning unit are electrically connected to the particle data storage unit.

15. A non-transitory computer-readable medium comprising machine-executable code that, upon execution by an analyzing device, causes the analyzing device to perform the method of claim 6.

16. An analyzing device comprising computer-executable instructions stored therein, the analyzing device is programmed to execute the computer-executable instructions to perform the method of claim 6.

\* \* \* \* \*